(12) United States Patent
Kim et al.

(10) Patent No.: US 7,163,805 B2
(45) Date of Patent: Jan. 16, 2007

(54) HUMAN SERUM ALBUMIN-TIMP2 FUSION PROTEIN, A POLYNUCLEOTIDE ENCODING THE SAME AND A METHOD OF PRODUCING THE HUMAN SERUM ALBUMIN-TIMP2 FUSION PROTEIN

(75) Inventors: Jeong-Yoon Kim, Daejeon (KR); Min-Young Kim, Daejeon (KR); Eun-Kyu Park, Daejeon (KR); Jae-Young Chang, Daejeon (KR); Hyun Ah Kang, Daejeon (KR)

(73) Assignees: Leadbio, Inc., Daejeon (KR); Angiolab, Inc., Daejeon (KR)

( * ) Notice: Subject to any disclaimer, the term of this patent is extended or adjusted under 35 U.S.C. 154(b) by 377 days.

(21) Appl. No.: 10/888,887

(22) Filed: Jul. 8, 2004

(65) Prior Publication Data

US 2005/0048627 A1 Mar. 3, 2005

Related U.S. Application Data

(63) Continuation-in-part of application No. PCT/KR03/00015, filed on Jan. 6, 2003.

(51) Int. Cl.
*C12P 21/02* (2006.01)
*C12N 1/21* (2006.01)
*C12N 1/19* (2006.01)
*C12N 15/63* (2006.01)
*C12N 5/10* (2006.01)
*C07K 14/765* (2006.01)
*C07H 21/04* (2006.01)

(52) U.S. Cl. ............. 435/69.1; 435/252.3; 435/254.11; 435/320.1; 435/325; 530/363; 536/23.4

(58) Field of Classification Search .................... None
See application file for complete search history.

(56) References Cited

U.S. PATENT DOCUMENTS 5,595,885 A 1/1997 Stetler-Stevenson et al.
5,643,752 A 7/1997 Hawkins et al.
5,876,969 A 3/1999 Fleer et al.

OTHER PUBLICATIONS

Wingfield et al., "Biophysical and Functional Characterization of Full-length, Recombinant Human Tissue Inhibitor of Metalloproteinases-2 (TIMP-2) Produced in *Escherichia coli*", The Journal of Biological Chemistry 1999, 274(30): 21362-21368.
Hajitou et al., "Down-Regulation of Vascular Endothelial Growth Factor by Tissue Inhibitor of Metalloproteinase-2: Effect on in Vivo Mammary Tumor", Cancer Research 2001, 61: 3450-3457.
Fernandez et al., "Structural and Functional Uncoupling of the Enzymatic and Angiogenic Inhibitory Activities of Tissue Inhibitor of Metalloproteinase-2 (TIMP-2)", The Journal of Biological Chemistry 2003, 278(42): 40989-40995.
Feldman et al., "Modulation of Tumor-host Interactions, Angiogenesis, and Tumor Growth by Tissue Inhibitor of Metalloproteinase 2 via a Novel Mechanism", Cancer Research 2004, 64: 4481-4486.
Rajan et al., "Presence of an N-Terminal Polyhistidine Tag Facilitates Stable Expression of an Otherwise Unstable N-Terminal Domain of Mouse Tissue Inhibitor of Metalloproteinase-1 in *Escherichia coli*", Pprotein Expression and Purification 1998, 13: 67-72.
Nomura et al., "Secretion by *Saccharomyces cerevisiae* of human apolipoprotein E as a fusion to serum albumin.", Biosci Biotechnol Biochem. Mar. 1995, 59(3): 532-4.
Cockett et al., "High level expression of tissue inhibitor of metalloproteinases in Chinese hamster ovary cells using glutamine synthetase gene amplification.", Biotechnology Jul. 1990, 8(7): 662-7.

*Primary Examiner*—Robert A. Wax
(74) *Attorney, Agent, or Firm*—JHK Law; Joseph Hyosuk Kim

(57) ABSTRACT

The present invention provides a human serum albumin-TIMP2 fusion protein having the amino acid sequence set forth in SEQ ID NO. 10, a polynucleotide encoding the same and a vector comprising the polynucleotide, a host cell transformed with the vector, a method for producing the human serum albumin-TIMP2 fusion protein and a pharmaceutical composition comprising the human serum albumin-TIMP2 fusion protein. The human serum albumin-TIMP2 fusion protein is stable and retains the activity of TIMP2, thus it can be used as a pharmaceutical composition to treat diseases related to angiogenesis and/or metastasis of cancer cells.

20 Claims, 7 Drawing Sheets pHSATIMP

HUMAN SERUM ALBUMIN-TIMP2 FUSION PROTEIN, A POLYNUCLEOTIDE ENCODING THE SAME AND A METHOD OF PRODUCING THE HUMAN SERUM ALBUMIN-TIMP2 FUSION PROTEIN

CONTINUATION DATA

This patent application is a continuation in part of PCT/KR03/00015 that was filed on Jan. 6, 2003.

TECHNICAL FIELD

The present invention relates to a fusion protein, and particularly, to a human serum albumin-TIMP2 fusion protein, a polynucleotide encoding the same, a vector comprising the polynucleotide, a transformed host cell comprising the vector, a pharmaceutical composition comprising the human serum albumin-TIMP2 fusion protein and a method for producing the human serum albumin-TIMP2 fusion protein.

BACKGROUND ART

Angiogenesis is the process of generating new capillary blood vessels. During angiogenesis, neovascularization is tightly regulated and activation thereof occurs in embryogenic development, tissue remodeling, wound healing, and periodic cycles of corpus luteum development (Folkman and Cotran, *Int. Rev. Exp. Pathol.*, 16, 207–248, 1976).

During the process of angiogenesis, capillary blood vessel endothelial cells start to proliferate from an existing vasculature. The endothelial cells grow very slowly as compared with other types of cells in a body. The proliferation of these cells is induced by pro-angiogenic cytokines, inflammation mediators, and activated proteolytic enzymes.

Failure to regulate angiogenesis leads to the development of several clinical syndromes or conditions. Pathological angiogenesis is involved in various diseases such as cancer in metastatic phase, arthritis, psoriasis, and retinopathy.

Not only reorganization of the blood vessel by migration, proliferation and differentiation of endothelial cells, but also degradation of an extracellular matrix is required for angiogenesis. One of the major events for inducing angiogenesis is a breakdown of the extracellular matrix before the formation of the capillary blood vessels. One of the most important enzymes which are involved in the matrix degradation is matrix metalloproteinase (MMP), a family of over 20 proteins. MMPs are endopeptidases, which degrade or proteolyze various components of the extracellular matrix such as collagen, proteoglycan, and gelatin.

An MMP's activity is modulated by an endogenous substance called Tissue Inhibitors of Metalloproteinases (TIMP) (Liotta and Stetler-Stevenson, *Semin. Cancer. Biol.* 1(2), 99–106, 1990; Liotta et al., *Cell*, 64(2), 327–336, 1991). The proteins in the TIMP family are classified as tumor suppressor proteins and four proteins have been identified as members of this family.

TIMP2, one of the four identified proteins in TIMP family, is able to bind to pro- and active form of MMP-2. Since TIMP2 inhibits all the activated forms of MMPs, TIMP2 acts as a key inhibitor molecule in angiogenesis and cancer metastasis. For example, tumor cell growth and metastasis were inhibited by a gene therapy with TIMP2 in experimental animals (Hajitou et al., *Cancer Res.*, 61, 3450–3457, 2001; Li et al., *Human Gene Ther.* 12, 515–526, 2001; Sacco et al., *Gene Ther.*, 8, 67–70, 2001). However, studies with TIMP2 were very limited due to a very limited amount of the protein existing in a biological system. Therefore, it is indispensable to develop a recombinant technique for overexpressing the TIMP-2 protein in vitro.

Although *E. coli* is a preferred host in recombinant DNA technology for producing large quantities of heterologous proteins economically, certain foreign proteins expressed in large quantities from *E. coli* are precipitated as inclusion bodies. Recovery of a biologically active protein from these inclusion bodies has presented critical problems and the recovered proteins are often biologically inactive because they are folded into a three-dimensional conformation different from that of native protein. Since TIMP2 has 6-disulfide linkages, it is very complicated to refold denatured TIMP2 into its correct, biologically active conformation.

As a eukaryote, yeast is a suitable host organism for a high-level production of secreted soluble cytosolic proteins of human origin. Indeed, many kinds of pharmaceutically important proteins have been expressed in yeast. Yeast is able to splice out introns and transport proteins through secretory pathways as higher eukaryotes do. Especially, *Saccharomyces cerevisiae*, the molecular and cellular biology of which has been intensively studied, has been exploited as a host for heterologous protein production since essential elements for gene expression such as strong and regulable promoters, vectors, and genetic markers are well developed (Romanos et al., *Yeast*, 8, 423–488, 1992). Moreover, its use in food fermentation for thousands of years proved that *S. cerevisiae* causes no harm to human beings and the processes for the production of therapeutic proteins using yeast acquired GRAS (generally recognized as safe) status. Altogether, these features make *S. cerevisiae* one of the most suitable organisms for heterologous gene expression.

Despite many advantages of yeast expression systems, a number of proteins are neither expressed in a large quantity nor secreted efficiently in yeast for unknown reasons. When human TIMP2 is expressed in yeast, for example in *S. cerevisiae*, the expression level is extremely low.

Human serum albumin (HSA) consisting of 585 amino acids is the most abundant protein in plasma, representing about 60% of total plasma proteins. A major function of serum albumin is to maintain a natural osmotic pressure of plasma and to transport sparingly soluble substances throughout the body. Serum albumin also functions as a carrier of endogenous and exogenous molecules, and for many years it has been thought to be devoid of any enzymatic function. However, recently, it has been found that it acts as dihydrotestosterone enolase and phospholipid cysteine peroxidase (Drmanovic et al., *Anticancer Res.* 19(5B), 4113–4124, 1999; Hurst et al., *Biochem J.*, 338(Pt3), 723–728, 1999). Despite these findings, exogenously administered modified serum albumins, for example recombinant therapeutic proteins fused to serum albumin, are not likely to contribute significantly to the total albumin pool because of the relative abundance of albumin in plasma. Furthermore, human serum albumin is a very stable protein displaying an in vivo half-life of 19 days in the adult human (Sterling, K., *J. Clin. Invest.*, 30, 1228, 1957).

DISCLOSURE OF THE INVENTION

It is an object of the present invention to provide a human serum albumin-TIMP2 fusion protein.

It is another object of the present invention to provide a polynucleotide encoding the human serum albumin-TIMP2 fusion protein.

It is another object of the present invention to provide a vector comprising a polynucleotide encoding a human serum albumin-TIMP2 fusion protein.

It is another object of the present invention to provide a transformed host cell with a vector comprising a polynucleotide encoding the human serum albumin-TIMP2 fusion protein.

It is another object of the present invention to provide a method for producing a human serum albumin-TIMP2 fusion protein.

It is yet another object of the present invention to provide a pharmaceutical composition comprising a human serum albumin-TIMP2 fusion protein.

The present invention provides a human serum albumin-TIMP2 fusion protein having the amino acid sequence of SEQ ID NO. 10. The fusion protein has an activity of inhibiting the MMP enzyme activity and angiogenesis. The molecular weight of the fusion protein is about 87.6 kDa. The fusion protein is made by fusing the carboxyl terminus of a human serum albumin to the amino terminus of TIMP2. When the fusion protein is linked to secretory signal sequence, it can be secreted to a medium more efficiently than the TIMP2. Moreover, the fusion protein is more stable than TIMP2 by being fused to a human serum albumin.

The present invention also provides a polynucleotide encoding a human serum albumin-TIMP2 fusion protein having the amino acid sequence of SEQ ID NO. 10. Preferably, the polynucleotide is a polynucleotide having nucleotide sequence set forth in SEQ ID NO. 3.

The present invention also provides a vector comprising a polynucleotide encoding a human serum albumin-TIMP2 fusion protein having the amino acid sequence of SEQ ID NO. 10. Preferably, the polynucleotide is a polynucleotide having nucleotide sequence set forth in SEQ ID NO. 3. The vector may include any element to establish a conventional function as a vector, for example, promoter, terminator, selection marker, and origin of replication. The promoter can be constitutive or regulative, and is selected from, for example, promoters of genes for galactokinase (GAL1), uridylyltransferase (GAL7), epimerase (GAL10), phosphoglycerate kinase (PGK), glyceraldehyde-3-phosphate dehydrogenase (GPD), alcohol dehydrogenase (ADH), and the like. The vector may further include a polynucleotide encoding a secretory signal sequence to secrete the fusion protein into a medium. The polynucleotide includes a polynucleotide encoding a secretory signal sequence which is, for example, a polynucleotide encoding a human serum albumin presequence having the nucleotide sequence set forth in SEQ ID. 2. Generally, the secretory signal sequence guides heterologous proteins through the secretory pathways of a host cell, for example, a yeast cell and finally to the culture medium. Preferably, the vector is a pHSATIMP. Table 1 describes the components of pHSATIMP. FIG. 1 is a schematic representation of the pHSATIMP plasmid.

TABLE 1

| pHSATIMP | |
|---|---|
| Promoter | GAL10 promoter (SEQ ID NO. 1) |
| Signal sequence | HSA signal sequence (SEQ ID NO. 2) |
| Structural gene | HSA-TIMP2 fusion gene (SEQ ID NO. 3) |
| Terminator | GAL7 terminator (SEQ ID NO. 4) |
| Selection marker | URA3 gene |
| Origin of replication | 2 μm |

The present invention also provides a host cell transformed with a vector comprising a polynucleotide encoding a human serum albumin-TIMP2 fusion protein having the amino acid sequence of SEQ ID NO. 10. Preferably, the polynucleotide is a polynucleotide having nucleotide sequence set forth in SEQ ID NO. 3. The host cell for the expression of the said polynucleotide, SEQ ID NO. 3, can be any cell, including yeasts, that can be used for the heterologous gene expression. As regards yeasts, preferred genera are *Saccharomyces, Pichia, Hansenula, Yarrowia, Kluyveromyces*, and *Schizosaccharomyces*. One example of the transformed host cell is *S. cerevisiae* JY28 [a strain (MAT pep4::HIS3 prb-1.6R can1 his3-20 ura3-52) carrying pHSA-TIMP] (KCTC 10131BP).

The present invention also provides a method for producing a human serum albumin-TIMP2 fusion protein by cultivating a host cell transformed with a vector comprising a polynucleotide encoding a human serum albumin-TIMP2 fusion protein having the amino acid sequence of SEQ ID NO. 10 in a suitable medium to produce the fusion protein and recovering the fusion protein. Preferably, the polynucleotide is a polynucleotide having nucleotide sequence set forth in SEQ ID NO. 3. One example of the transformed host cell is *S. cerevisiae* JY28 [a strain (MAT pep4::HIS3 prb-1.6R can1 his3-20 ura3-52) carrying pHSATIMP] (KCTC 10131BP). The medium varies depending on a selected host cell, and includes a conventional medium used for cultivating the selected host cell. For example, if the host cell is *S. cerevisiae* JY28 [a strain (MATpep4::HIS3 prb-1.6R can1 his3-20 ura3-52) carrying pHSATIMP] (KCTC 10131BP), a minimal medium containing 6.7 grams of yeast nitrogen base (without amino acids) (YNB) (Difco), 20 grams of glucose, and 20 grams of agar per liter can be used for the maintenance. The transformed host cell can be induced to produce the human HSA-TIMP2 by cultivating for 2 days at 30° C. in an induction medium composed of 10 grams of yeast extract (Difco), 20 grams of Bacto-peptone (Difco), 10 grams of glucose, and 20 grams of galactose per liter. The host cell transformed with the vector containing the polynucleotide, SEQ ID NO. 3, expresses and secretes the recombinant fusion protein of about 87.6 kDa in size. The recombinant fusion protein defines human TIMP2 protein fused with human serum albumin, retaining the biological activity of human TIMP2 protein.

Conventional separation and purification methods for protein can be used to purify the human serum albumin-TIMP2 fusion protein of the present invention. For example, a salting out, a dialysis, an ion chromatography and an affinity chromatography can be used. When *S. cerevisiae* JY28 [a strain (MATpep4::HIS3 prb-1.6R can1 his3-20 ura3-52) carrying pHSATIMP] (KCTC 10131BP) was used, the final concentration of the fusion protein in culture supernatant was about 30–50 mg per liter in a flask culture. Yeast strains including *S. cerevisiae* are known to secrete only a little amount of TIMP2, but the secretion efficiency was increased more than 50- to 100-folds by fusing TIMP2 with human serum albumin protein in the present invention.

The present invention also provides a pharmaceutical composition comprising a pharmaceutically effective amount of the human serum albumin-TIMP2 fusion protein and a pharmaceutically acceptable diluent or carrier. The diluent or carrier can be any material conventionally used for a pharmaceutical composition comprising a protein. The recombinant fusion protein in the present invention not only inhibits the activity of MMPs (FIG. 4) but also suppresses the tube formation of human vein umbilical cells (FIG. 5). Therefore, the human serum albumin-TIMP2 fusion protein of the present invention retains biological activity of the TIMP2 protein, and the fusion protein is expected to be pharmaceutically useful without any undesirable side effects because serum albumin used as a fusion partner is known to be the most abundant protein in plasma. Thus, the fusion protein can be used as an anti-angiogenic protein. In particular, the fusion protein is a potent therapeutic agent to treat diseases related to angiogenesis and/or metastasis of cancer cells and may be more useful than TIMP2 itself because of its prolonged in vivo stability endowed by its fusion partner, human serum albumin.

DETAILED DESCRIPTION OF THE INVENTION

Figure 1:
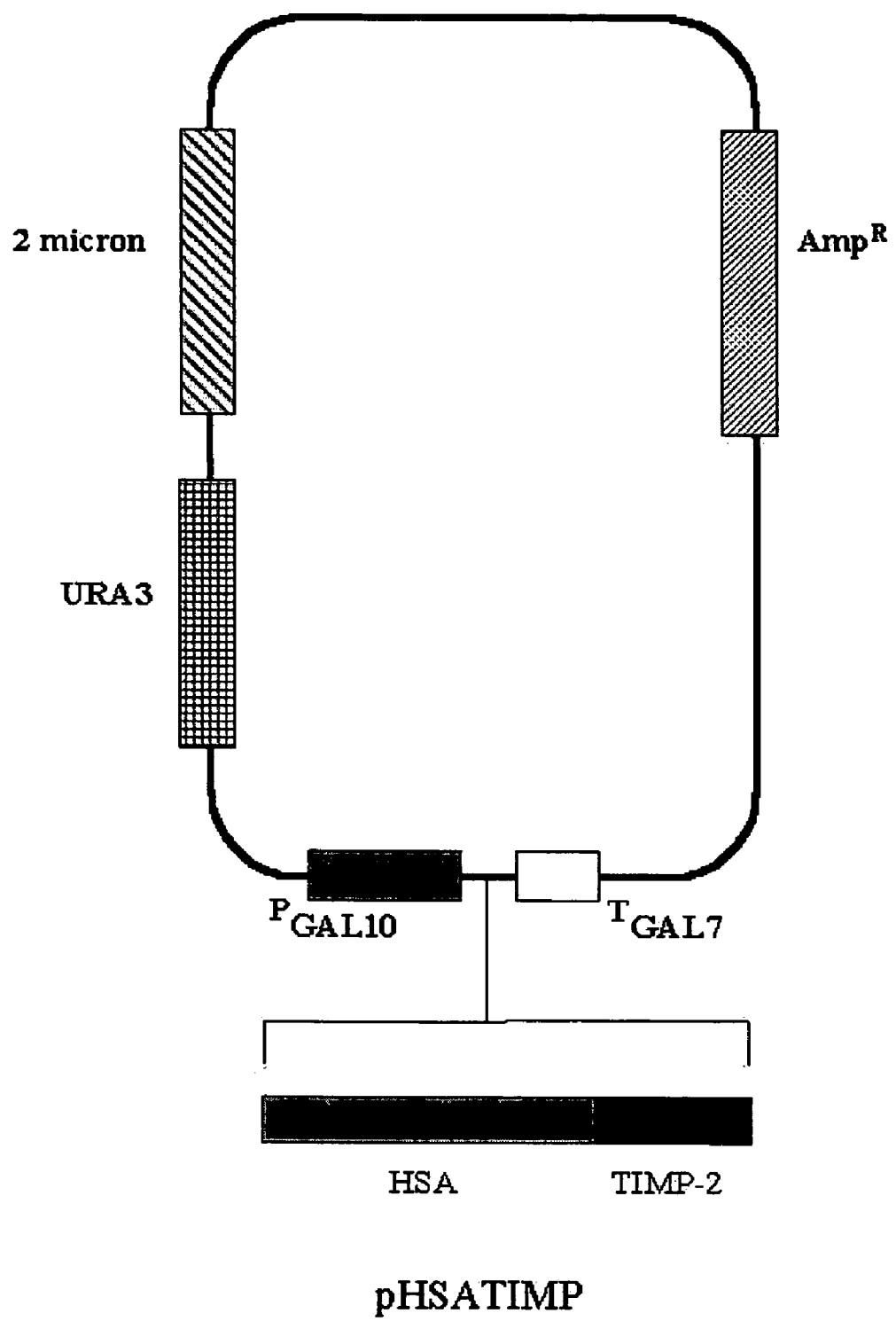
FIG. 1 is a schematic representation of the pHSATIMP plasmid.

As used herein, "amino acid" and "amino acids" refer to all naturally occurring L-α-amino acids. This definition is meant to include norleucine, ornithine, and homocysteine.

As used herein, in general, the term "amino acid sequence variant" refers to molecules with some differences in their amino acid sequences as compared to a reference (e.g. native sequence) polypeptide. The amino acid alterations may be substitutions, insertions, deletions or any desired combinations of such changes in a native amino acid sequence.

Substitutional variants are those that have at least one amino acid residue in a native sequence removed and a different amino acid inserted in its place at the same position. The substitutions may be single, where only one amino acid in the molecule has been substituted, or they may be multiple, where two or more amino acids have been substituted in the same molecule.

Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Also included within the scope of the invention are proteins or fragments or derivatives thereof which exhibit the same or similar biological activity and derivatives which are differentially modified during or after translation, e.g., by glycosylation, proteolytic cleavage, linkage to an antibody molecule or other cellular ligand, and so on.

Insertional variants are those with one or more amino acids inserted immediately adjacent to an amino acid at a particular position in a native amino acid sequence. Immediately adjacent to an amino acid means connected to either the α-carboxy or α-amino functional group of the amino acid.

Deletional variants are those with one or more amino acids in the native amino acid sequence removed. Ordinarily, deletional variants will have one or two amino acids deleted in a particular region of the molecule.

In one aspect, the polypeptide variants of the present invention may contain any number of amino acids or alterations of amino acids in the gap junction polypeptide, including substitutions and/or insertions and/or deletions in any region of the polypeptide molecule. In particular, the polypeptide variant includes a sequence that is at least about 70%, 75%, 80%, 85%, 90%, 95%, 96%, 97%, 98% or 99% identical to the polypeptide sequence represented by SEQ ID NO. 10 and the presence of the variations do not hinder the angiogenesis modulating function corresponding to the native serum albumin-TIMP2 fusion polypeptide.

As used herein, "angiogenesis" is meant the growth of a new blood vessel in which the proliferation and/or migration of an endothelial cell is a key step. By "inhibiting angiogenesis" is meant the inhibition of any of the steps of the process of angiogenesis that includes, without limitation, proliferation and/or migration of endothelial cells. By "promoting angiogenesis" is meant the promotion of any of the steps of the process of angiogenesis that includes, without limitation, proliferation and/or migration of endothelial cells.

As used herein, "angiogenesis related disease" refers to those diseases that are caused by either the proliferation of blood vessels or inhibition of formation of blood vessels.

As used herein, "carriers" include pharmaceutically acceptable carriers, excipients, or stabilizers which are non-toxic to the cell or mammal being exposed thereto at the dosages and concentrations employed. Often the pharmaceutically acceptable carrier is an aqueous pH buffered solution. Examples of pharmaceutically acceptable carriers include without limitation buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

As used herein, "effective amount" is an amount sufficient to effect beneficial or desired clinical or biochemical results. An effective amount can be administered one or more times. For purposes of this invention, an effective amount of an inhibitor polypeptide is an amount that is sufficient to palliate, ameliorate, stabilize, reverse, slow or delay the progression of an angiogenesis-related disease. In a preferred embodiment of the invention, the "effective amount" is defined as an amount of compound capable of modulating angiogenesis or treating an angiogenesis-related disease.

As used herein, "host cell" includes an individual cell or cell culture which can be or has been a recipient of a vector of this invention. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo with a vector comprising a polynucleotide encoding a serum albumin-TIMP2 polypeptide.

As used herein, "serum albumin" refers generally to serum albumin obtained from any mammalian source so long as it is fused to the TIMP2 protein thereby creating a fusion polypeptide. Source of the serum albumin may be from any mammal, such as bovine or human, and may be from any stage of life of such a mammal as well. Preferably, human serum albumin may be used. In this regard, serum albumin-TIMP2 may be alternatively written as SA-TIMP2, and in particular, human serum albumin-TIMP2 maybe alternatively written as HSA-TIMP2.

As used herein, "treatment" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. "Treatment" refers to both therapeutic treatment and prophylactic or preventative measures. Those in need of treatment include those already with the disorder as well as those in which the disorder is to be prevented. "Palliating" a disease means that the extent and/or undesirable clinical manifestations of a disease state are lessened and/or the time course of the progression is slowed or lengthened, as compared to a situation without treatment.

As used herein, "vector" means a carrier that can contain or associate with specific nucleic acid sequences, which functions to transport the specific nucleic acid sequences into a cell. Examples of vectors include plasmids and infective microorganisms such as viruses, or non-viral vectors such as ligand-DNA conjugates, liposomes, lipid-DNA complexes. It may be desirable that recombinant DNA molecule comprising serum albumin-TIMP2 DNA sequence is operatively linked to an expression control sequence to form expression vectors capable of expressing serum albumin-TIMP2 polypeptide. The transfected cells may be cells derived from the patient's normal tissue, the patient's diseased tissue, or may be non-patient cells.

Gene Therapy

The present invention also encompasses gene therapy whereby the polynucleotide encoding serum albumin-TIMP2 polypeptide is regulated in a patient. Various methods of transferring or delivering DNA to cells for expression of the gene product protein, otherwise referred to as gene therapy, are disclosed in Gene Transfer into Mammalian Somatic Cells in vivo, N. Yang, Crit. Rev. Biotechn. 12(4): 335–356 (1992). Gene therapy encompasses incorporation of DNA sequences into somatic cells or germ line cells for use in either ex vivo or in vivo therapy. Gene therapy functions to replace genes, augment normal or abnormal gene function, and to combat infectious diseases and other pathologies.

Strategies for treating these medical problems with gene therapy include therapeutic strategies such as adding a functional gene to either replace the function of the defective gene or to augment a slightly functional gene; or prophylactic strategies, such as adding a gene for the product protein that will treat the condition or that will make the tissue or organ more susceptible to a treatment regimen. As an example of a prophylactic strategy, a polynucleotide encoding serum albumin-TIMP2 polypeptide may be placed in a patient and thus prevent or promote occurrence of angiogenesis.

Gene transfer methods for gene therapy fall into three broad categories-physical (e.g., electroporation, direct gene transfer and particle bombardment), chemical (lipid-based carriers, or other non-viral vectors) and biological (virus-derived vector and receptor uptake). For example, non-viral vectors may be used which include liposomes coated with DNA. Such liposome/DNA complexes may be directly injected intravenously into the patient. It is believed that the liposome/DNA complexes are concentrated in the liver where they deliver the DNA to macrophages and Kupffer cells. These cells are long lived and thus provide long term expression of the delivered DNA. Additionally, vectors or the "naked" DNA of the gene may be directly injected into the desired organ, tissue or tumor for targeted delivery of the therapeutic DNA.

Gene therapy methodologies can also be described by delivery site. Fundamental ways to deliver genes include ex vivo gene transfer, in vivo gene transfer, and in vitro gene transfer. In ex vivo gene transfer, cells are taken from the patient and grown in cell culture. The DNA is transfected into the cells, the transfected cells are expanded in number and then reimplanted in the patient. In in vitro gene transfer, the transformed cells are cells grown in culture, such as tissue culture cells, and not particular cells from a particular patient. These "laboratory cells" are transfected, the transfected cells are selected and expanded for either implantation into a patient or for other uses.

Therapeutic Composition

The present invention includes a method of treating an angiogenesis mediated disease by administering a therapeutically effective amount of serum albumin-TIMP2 polypeptide, or a biologically active fragment thereof, or different sets of combinations of serum albumin-TIMP2 polypeptide fragments that collectively possess anti-angiogenic activity. Angiogenesis mediated diseases include, but are not limited to, solid tumors; blood born tumors such as leukemias; tumor metastasis; benign tumors, for example hemangiomas, acoustic neuromas, neurofibromas, trachomas, and pyogenic granulomas; rheumatoid arthritis; psoriasis; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome; myocardial angiogenesis; plaque neovascularization; telangiectasia; hemophiliac joints; angiofibroma; and wound granulation.

Serum albumin-TIMP2 polypeptide may be also used in combination with other compositions and procedures for the treatment of diseases. For example, a tumor may be treated conventionally with surgery, radiation or chemotherapy combined with the serum albumin-TIMP2 polypeptide and then the serum albumin-TIMP2 polypeptide may be subsequently administered to the patient to extend the dormancy of micrometastases and to stabilize and inhibit the growth of any residual primary tumor. Additionally, and in particular, serum albumin-TIMP2 polypeptide may be combined with pharmaceutically acceptable excipients, and optionally sustained-release matrix, such as biodegradable polymers, to form therapeutic compositions.

A sustained-release matrix, as used herein, is a matrix made of materials, usually polymers, which are degradable by enzymatic or acid/base hydrolysis or by dissolution. Once inserted into the body, the matrix is acted upon by enzymes and body fluids. The sustained-release matrix desirably is chosen from biocompatible materials such as liposomes, polylactides (polylactic acid), polyglycolide (polymer of glycolic acid), polylactide co-glycolide (co-polymers of lactic acid and glycolic acid) polyanhydrides, poly(ortho)esters, polyproteins, hyaluronic acid, collagen, chondroitin sulfate, carboxylic acids, fatty acids, phospho-lipids, polysaccharides, nucleic acids, polyamino acids, amino acids such as phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

The angiogenesis-modulating therapeutic composition of the present invention may be a solid, liquid or aerosol and may be administered by any known route of administration. Examples of solid therapeutic compositions include pills, creams, and implantable dosage units. The pills may be administered orally, the therapeutic creams may be administered topically. The implantable dosage units may be administered locally, for example at a tumor site, or which may be implanted for systemic release of the therapeutic angiogenesis-modulating composition, for example subcutaneously. Examples of liquid composition include formulations adapted for injection subcutaneously, intravenously, intraarterially, and formulations for topical and intraocular administration. Examples of aersol formulation include inhaler formulation for administration to the lungs.

The dosage of the serum albumin-TIMP2 polypeptide of the present invention will depend on the disease state or condition being treated and other clinical factors such as weight and condition of the human or animal and the route of administration of the compound.

The serum albumin-TIMP2 polypeptide formulations include those suitable for oral, rectal, ophthalmic (including intravitreal or intracameral), nasal, topical (including buccal and sublingual), intrauterine, vaginal or parenteral (including subcutaneous, intraperitoneal, intramuscular, intravenous, intradermal, intracranial, intratracheal, and epidural) administration. The serum albumin-TIMP2 polypeptide formulations may conveniently be presented in unit dosage form and may be prepared by conventional pharmaceutical techniques.

Such techniques include the step of bringing into association the active ingredient and the pharmaceutical carrier(s) or excipient(s). In general, the formulations are prepared by uniformly and intimately bringing into association the active ingredient with liquid carriers or finely divided solid carriers or both, and then, if necessary, shaping the product.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

BEST MODE FOR CARRYING OUT THE INVENTION

The following examples are intended to further illustrate the present invention. However, these examples are presented only for a better understanding of the present invention without limiting its scope.

EXAMPLE 1

Construction of the Recombinant Expression Vector

In the present example, pHSATIMP containing GAL10 promoter, HSA signal sequence, HSA structural gene, TIMP2 structural gene, and GAL7 terminator was prepared. The gene for human serum albumin was amplified by PCR. The template was the HSA gene in the plasmid pHSA (LeadBio, Inc) and the primers used were SEQ ID NO. 5 (forward primer with the recognition sequence for EcoRI) and SEQ ID NO. 6 (backward primer containing 15 mers that are complementary to the primer of SEQ ID NO. 7). The gene for human TIMP2 was also amplified by PCR. The template was the TIMP2 gene in the plasmid pMY2 (AngioLab, Inc) and the primers used were SEQ ID NO. 7 (forward primer) and SEQ ID NO. 8 (backward primer with the recognition sequence for HindIII). The 15 mers of 3' terminal sequence of the amplified human serum albumin gene and the 15 mers of 5' terminal sequence of the TIMP2 gene are complementary to each other. Thus, in-frame fusion of the human serum albumin and TIMP2 genes could be made by PCR using SEQ ID NO. 5 and SEQ ID NO. 8 as primers. The PCR product treated with restriction enzymes EcoRI and HindIII were ligated with the vector pHSA cut with EcoRI and HindIII, resulting in the recombinant vector, pHSATIMP.

EXAMPLE 2

Construction of Transformant

The plasmid, pHSATIMP prepared in Example 1 was introduced into *S. cerevisiae* Y2805 (MATpep4::HIS3 prb-1.6R can1 his3-20 ura3-52) by lithium acetate method (Ito et al., *J. Bacteriol.* 153, 163–168, 1983). The selected transformants were further tested by further growing them on a synthetic complete medium without uracil. The finally selected transformant was named *S. cerevisiae* JY28 (Y2805/pHSATIMP) and deposited in KCTC (Korean Collection for Type Cultures) 10131 BP on Dec. 3, 2001.

EXAMPLE 3

Expression of the Human Serum Albumin and TIMP2 Fusion Protein

Figure 2:
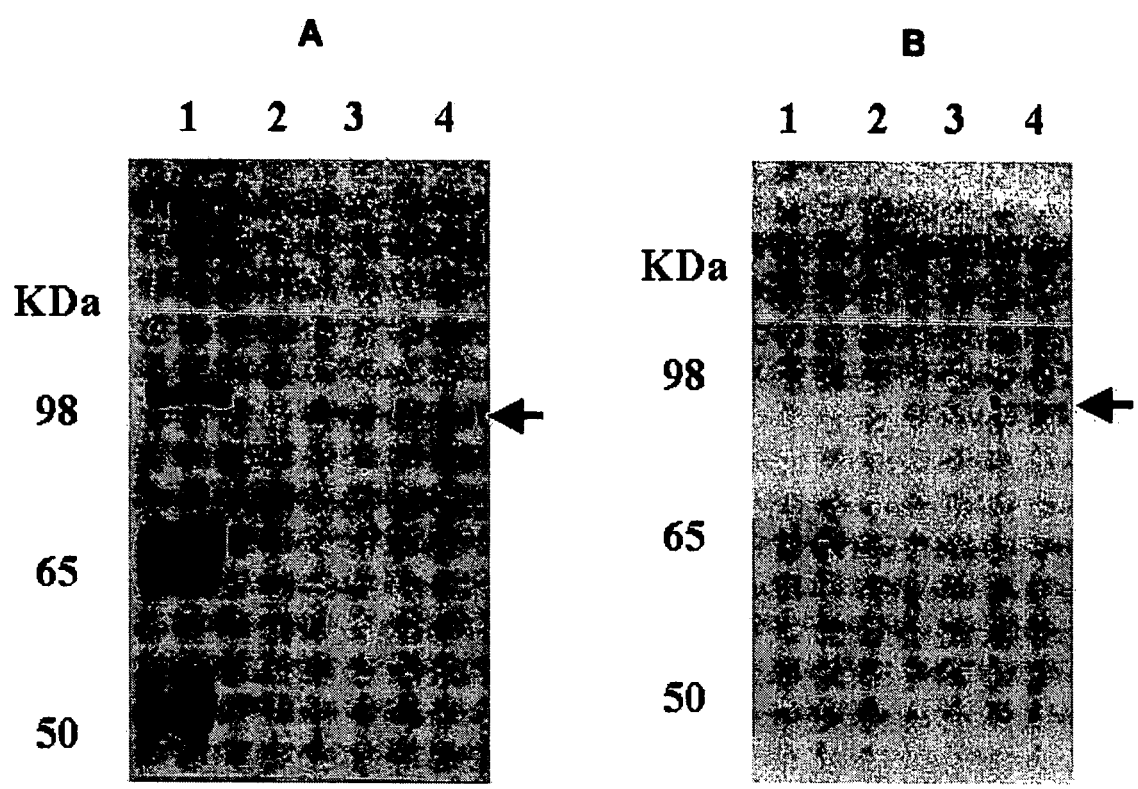
FIGS. 2A–2B show SDS-PAGE and Western blotting results of the culture supernatants of S. cerevisiae JY28 (Y2805/pHSATIMP).

The transformant obtained in Example 2 was grown for 2 days at 30° C. in 50 ml of YPDG medium (1% Yeast extract, 2% Proteose-peptone, 1% glucose, 2% galactose). When glucose in the medium was depleted, GAL10 promoter was turned on by galactose and the HSA-TIMP2 fusion protein was expressed and secreted. Culture supernatants (20 µl) taken after 24 and 48 hours were analyzed on an SDS-PAGE gel by staining the gel with coomassie blue or after immunoblotting using a rabbit polyclonal serum directed against HSA. FIG. 2 displays the SDS-PAGE and Western blotting results of the culture supernatants of *S. cerevisiae* JY28 (Y2805/pHSATIMP). FIG. 2A is a result of SDS-PAGE of the culture supernatants with Coomassie blue staining. FIG. 2B is a result of Western blotting with a rabbit polyclonal serum directed to a human serum albumin. Lanes 1, 2, 3, and 4 indicate a molecular weight marker, a supernatant(10 µl) of a control strain (Y2805) culture after 48 hours of growth; a supernatant(10 µl) of a JY28 (Y2805/pHSATIMP) culture after 24 hours of growth, and a supernatant(10 µl) of a JY28 (Y2805/pHSATIMP) culture after 48 hours of growth, respectively. The HSA-TIMP2 fusion protein having the size of 87.6 kDa is clearly shown in lanes 3 and 4.

EXAMPLE 4

Purification of the Recombinant HSA-TIMP2 Protein

Figure 3:
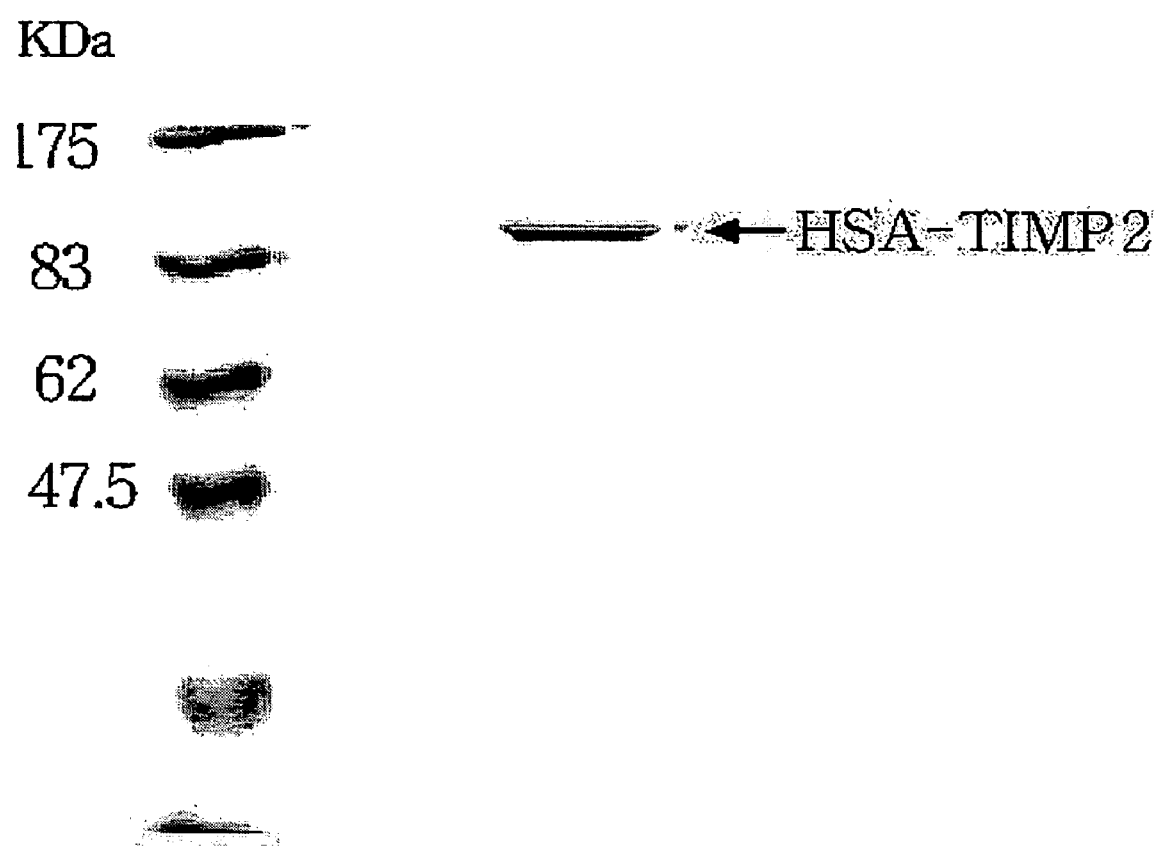
FIG. 3 shows the SDS-PAGE for purified recombinant HSA-TIMP2 fusion protein.

In order to purify the HSA-TIMP2, yeast culture media of Example 3 was recovered after centrifugation at 10,000×g for 10 min. Proteins in the supernatant were precipitated with 70% of ammonium sulfate solution. Pellets were collected by centrifugation for 30 min at 15,000×g, and redissolved in 50 mM HEPES buffer (pH 8.0). After removal of ammonium sulfate by dialysis, the concentrated protein solution was subjected to DEAE-sepharose (Pharmacia) column chromatography. The column was washed with 50 mM HEPES buffer, pH 8.0, and bound proteins were eluted with linear gradient of 0.1–0.5 M NaCl solution. HSA-TIMP2 was eluted at 0.24 M of NaCl, the protein was analyzed on SDS-PAGE. As shown in FIG. 3, the molecular size of the purified recombinant HSA-TIMP2 fusion protein was 87.6 kDa. About 20 mg of the HSA-TIMP2 was obtained from 1L of culture media.

EXAMPLE 5

Effect of the Recombinant HSA-TIMP2 on Matrix Metalloproteinase Activity (1) Preparation of MMP MMP-2 cDNA (GENEBANK No. XM_048244) was cloned and prepared from insect cells (Sf21 insect cell) by using a Baculovirus system.

The obtained MMP-2 cDNA was cloned to a pBlueBac4.5 transfer vector (Invitrogen, Cat no. V1995-20), and then transfected to Sf21 cells with a Bac-N-Blue Transfection Kit (Invitrogen, Cat no. K855-01). Sf21 cells were cultured in TNM-FH media (Sigma, St. Louis, Mo., U.S.A) containing 10% fetal bovine serum at 27° C., then harvested and re-suspended at a concentration of $10^7$ cell/ml. The cell suspension was incubated with a virus containing the cloned gene for 1 hr at room temperature. Infected Sf21 cells were grown for 72 hrs and the medium was recovered, and the MMP-2 was purified using a gelatin-sepharose affinity column (Sigma, G5384) chromatography.

(2) Inhibition of MMP Activity

In order to investigate MMP inhibition by the recombinant HSA-TIMP2 fusion protein, MMP activity was assayed by a spectrofluorometric method using Perkin-Elmer LS50B.

Purified MMP-2 was used after activation with 1 mM APMA before assay. The substrate for MMP-2 was MCA-Pro-Leu-Gly-Leu-Dap(Dnp)-Ala-Arg-$NH_2$ (Bachem, Cat. No. M-1895).

For control, 2 ml of reaction buffer (50 mM Tricine, pH 7.5, 10 mM $CaCl_2$, 200 mM NaCl) comprising DMSO, 10 nM of MMP-2 and 10 μM of substrate was prepared in a cuvette, and fluorescence intensity was measured for 5–10 min. at room temperature with a spectrofluorometer under an excitation wavelength of 328 nm and an emission wavelength of 393 nm.

HSA-TIMP2 was added to a reaction buffer containing a substrate and MMP-2, and fluorescence intensity was measured in the same manner.

Figure 4:
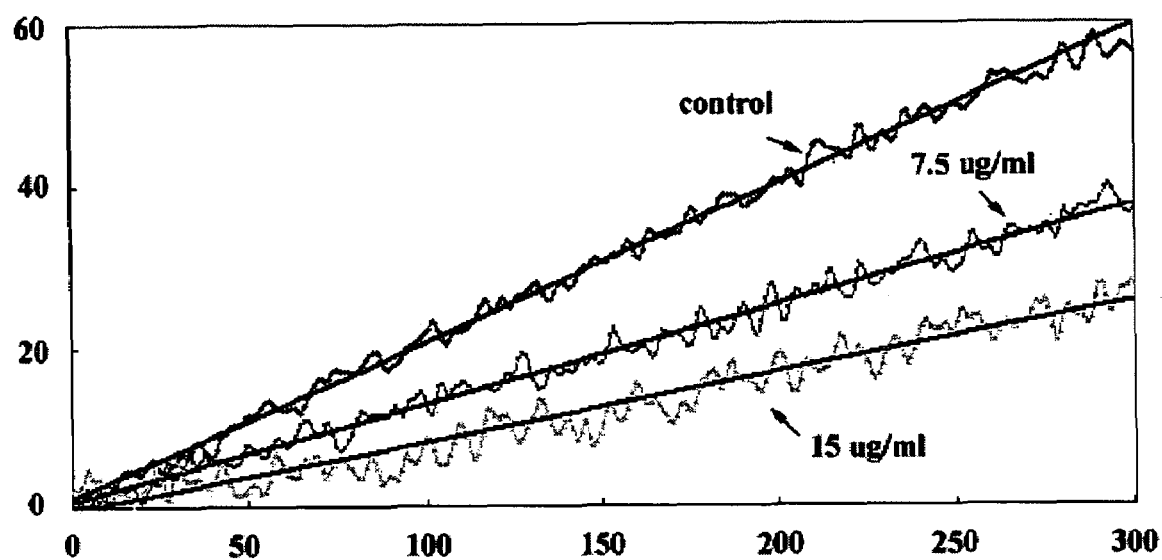
FIG. 4 shows the inhibitory activity of the purified recombinant HSA-TIMP2 protein on MMP-2.

FIG. 4 shows the inhibitory activity of the purified recombinant HSA-TIMP2 fusion protein on MMP-2. As shown in FIG. 4, 7.5 μg/ml and 15 μg/ml of HSA-TIMP2 inhibited about 37% and 55% of MMP-2 activity, respectively.

EXAMPLE 6

Effect of the Recombinant HSA-TIMP2 Fusion Protein on Tube Formation of HUVEC

The effect of the recombinant HSA-TIMP2 fusion protein on human endothelial cells was investigated to evaluate the biological effect of the HSA-TIMP2 of the present invention. Since MMPs are responsible for the degradation of extracellular matrix, TIMP2 is able to inhibit the formation of tubular network of vessel, which represents migration and differentiation of endothelial cell.

Blood vessel endothelial cells, human umbilical vein endothelial cells (HUVECs), were isolated from freshly obtained cords after a cesarean section according to Grants' method (Grants et al., *Cell*, 58, 933–943,1989). They were identified by immunocytochemical staining with anti-Factor VIII antibody. HUVECs cultured on Matrigel (BD Bioscience, Bedford, Mass., USA) were treated with 6.5 μg/ml of HSA-TIMP2, and further incubated at 37° C. for 8–16 hrs. For control, the procedure was repeated with a solution without the recombinant HSA-TIMP2 fusion protein.

Figure 5A:
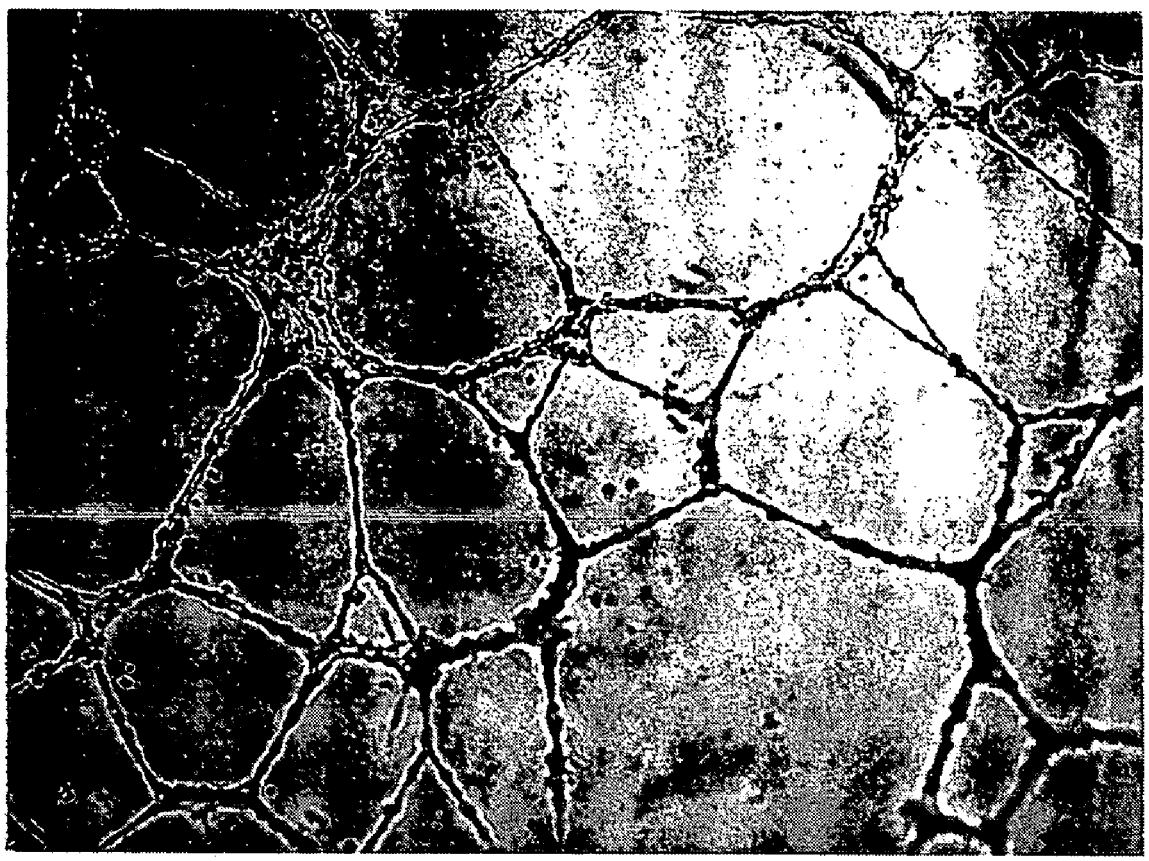
FIGS. 5A–5B show the effects of recombinant HSA-TIMP2 on the tube formation of human umbilical vein endothelial cells (HUVECs).
Figure 5B:
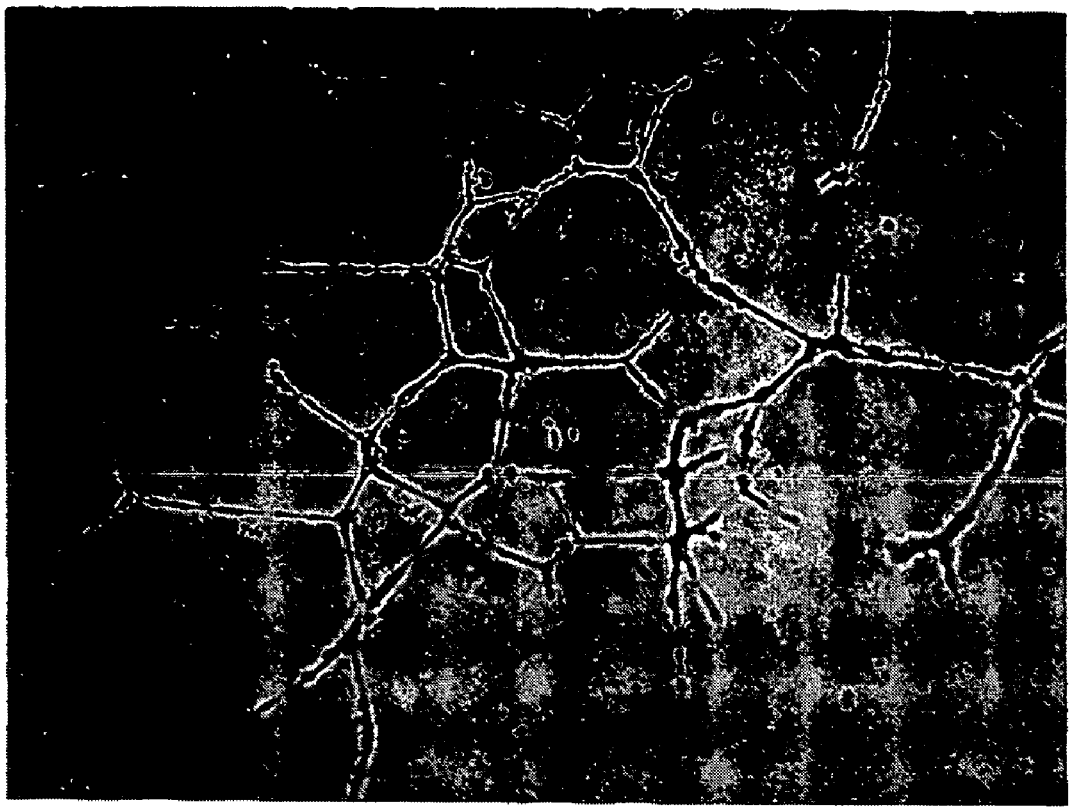

FIG. 5 shows the effect of the recombinant HAS-TIMP2 on a tube formation of human umbilical vein endothelial cells (HUVECs). FIG. 5A shows that a tubular network was formed as a process of neovascularization, when the HUVECs were grown on Matrigel. However, the microvascular network was disconnected when the HUVECs grown on Matrigel were treated with 6.5 μg/ml of HSA-TIMP2 (FIG. 5B). These data show that HSA-TIMP2 is able to inhibit angiogenesis by inhibiting MMP activity.

When the area of the tubular network of HUVECs was determined using an image analysis program, Image-Pro Plus® (Media Cybernetics, USA), the tube area after treatment of HSA-TIMP2 was about 19% as compared with the untreated control. That is, the tube formation was inhibited by 81% with 6.5 μg/ml of HSA-TIMP2 of the present invention.

EXAMPLE 7

Effect of the Recombinant HSA-TIMP2 Fusion Protein on in Vivo Angiogenesis (Mouse Matrigel Model)

Figure 6:
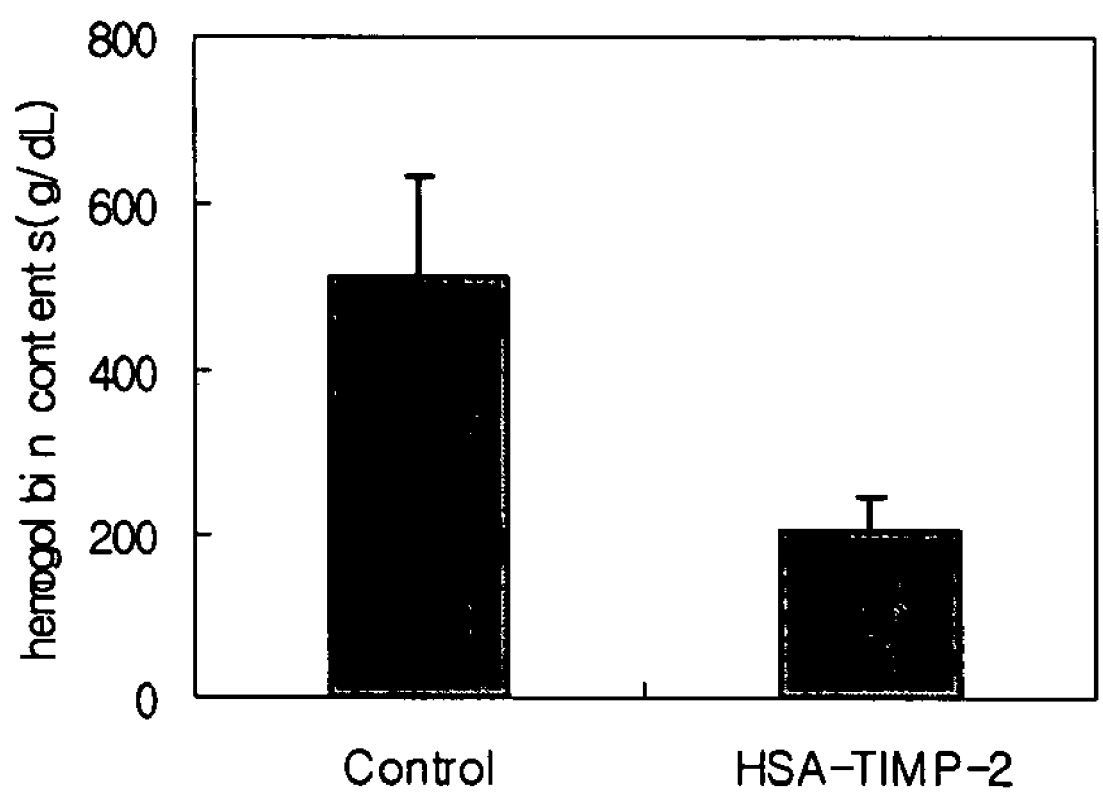
FIG. 6 shows the effect of the recombinant HSA-TIMP2 fusion protein on in vivo angiogenesis.

The effect of recombinant HSA-TIMP2 fusion protein on in vivo angiogenesis was examined using mouse Matrigel model. 6 week-old C57BL mice(Japan SLP Inc.) were injected subcutaneously with 0.4 ml of Matrigel (BD Biosciences, Bedford, Mass.) containing 50 ng/ml of bFGF and 60 units/ml of heparin using a 25 gauge needle. To each mouse 400 μg of recombinant HSA-TIMP2 fusion protein was injected intraperitoneally once a day for four days. The control animals receive PBS injection. At day 5 mice were sacrificed, and Matrigel plugs were recovered. Amount of hemoglobin contained in the Matrigel was measured using Drabkin's reagent kit 525 (Sigma, St Louis, Mo.) for the quantitation of blood vessel formation. The concentration of hemoglobin was calculated from a known amount of hemoglobin assayed in parallel and total hemoglobin content in Matrigel was determined. As shown in Table 2 and FIG. 6, the average of total hemoglobin content in the Matrigel of recombinant HSA-TIMP2-treated group were about 40% of that of the control group indicating that recombinant HSA-TIMP2 inhibited angiogenesis by 60%.

TABLE 2

| | Content of Hemoglobin (g/dl) |
|---|---|
| Control group | 511 ± 119 |
| HSA-TIMP2-treated group | 205 ± 42 |

Industrial Applicability

According to the human serum albumin-TIMP2 fusion protein of the present invention, it retains the biological activity of the TIMP2 and can be used as a pharmaceutically active component without any undesirable side effects.

According to the polynucleotide and the vector comprising the same of the present invention, it is able to express the human serum albumin-TIMP2 fusion protein of the invention.

According to the pharmaceutical composition of the present invention, it can be used as an anti-angiogenic protein or as a potent therapeutic agent to treat diseases related to angiogenesis and/or metastasis of cancer cells.

According to the method of the present invention, the human serum albumin-TIMP2 fusion protein of the present invention can be produced on a large scale by using a transformed host cell.

What is claimed is:

1. A serum albumin-TIMP2 fusion polypeptide.
2. The polypeptide according to claim 1, having the amino acid sequence set forth in SEQ ID NO. 10.
3. A polynucleotide encoding the polypeptide according to claim 1.
4. A polynucleotide encoding the polypeptide according to claim 2.
5. The polynucleotide of claim 4, having the nucleotide sequence set forth in SEQ ID NO. 3.
6. A vector comprising the polynucleotide according to claim 3.
7. A vector comprising the polynucleotide according to claim 4.
8. A vector comprising the polynucleotide according to claim 5.
9. The vector of claim 6, comprising a polynucleotide encoding a secretory signal sequence for extracellular secretion of a protein.
10. The vector of claim 9, wherein the secretory signal sequence comprises a polynucleotide encoding a human serum albumin presequence.
11. The vector of claim 6, wherein the vector is pHSA-TIMP.
12. A host cell comprising the vector according to claim 6.
13. A host cell comprising the vector according to claim 7.
14. A host cell comprising the vector according to claim 8.
15. The host cell of claim 12, which is a eukaryotic cell.
16. The host cell of claim 15, which is a fungal cell.
17. The host cell of claim 16, which is a yeast cell.
18. The host cell of claim 17, which is *S. cerevisiae* JY28 (KCTC 10131BP).
19. A method for producing serum albumin-TIMP2 fusion polypeptide comprising culturing the transformed host cell according to claim 12 in a suitable medium to produce the serum albumin-TIMP2 fusion protein and recovering the serum albumin-TIMP2 fusion protein.
20. A pharmaceutical composition comprising a pharmaceutically effective amount of a serum albumin-TIMP2 fusion protein and a pharmaceutically acceptable diluent or carrier thereof.

* * * * *

SEQUENCE LISTING

<160> NUMBER OF SEQ ID NOS: 10

<210> SEQ ID NO 1
<211> LENGTH: 507
<212> TYPE: DNA
<213> ORGANISM: Artificial Sequence
<220> FEATURE:
<223> OTHER INFORMATION: GAL10 promoter

<400> SEQUENCE: 1

```
atcgcttcgc tgattaatta ccccagaaat aaggctaaaa aactaatcgc attatcatcc      60
tatggttgtt aatttgattc gttcatttga aggtttgtgg ggccaggtta ctgccaattt     120
ttcctcttca taaccataaa agctagtatt gtagaatctt tattgttcgg accagtgcgg     180
cgcgaggcac atctgcgttt caggaacgcg accggtgaag acgaggacgc acggaggaga     240
gtcttccttc ggagggctgt cacccgctcg gcggcttcta atccgtactt caatatagca     300
atgagcagtt aagcgtatta ctgaaagttc caaagagaag gttttttttag gctaagataa     360 tggggctctt tacatttcca caacatataa gtaagattag atatggatat gtatatggat     420
atgtatatgg tggtaatgcc atgtaatatg attattaaac ttctttgcgt ccatccaaaa     480
aaaaagtaag aattttttgaa aattcaa                                         507
```

<210> SEQ ID NO 2
<211> LENGTH: 72
<212> TYPE: DNA
<213> ORGANISM: Artificial Sequence
<220> FEATURE:
<223> OTHER INFORMATION: HSA pre signal

<400> SEQUENCE: 2

```
atgaagtggg taacctttat ttcccttctt tttctcttta gctcggctta ttccaggggt      60
gtgtttcgtc ga                                                           72
```

<210> SEQ ID NO 3
<211> LENGTH: 2340
<212> TYPE: DNA
<213> ORGANISM: Artificial Sequence
<220> FEATURE:
<223> OTHER INFORMATION: HSA-TIMP2 fusion gene -continued

```
<400> SEQUENCE: 3
gatgcacaca agagtgaggt tgctcatcgg tttaaagatt tgggagaaga aaatttcaaa        60
gccttggtgt tgattgcctt tgctcagtat cttcagcagt gtccatttga agatcatgta       120
aaattagtca atgaagtaac tgaatttgca aaaacatgtg ttgctgatga gtcagctgaa       180
aattgtgaca aatcacttca tacccttttt ggagacaaat tatgcacagt tgcaactctt       240
cgtgaaacct atggtgaaat ggctgactgc tgtgcaaaac aagaacctga gagaaatgaa       300
tgcttcttgc aacacaaaga tgacaaccca aacctccccc gattggtgag accagaggtt       360
gatgtgatgt gcactgcttt tcatgacaat gaagagacat ttttgaaaaa atacttatat       420
gaaattgcca aagacatcc ttactttat gccccggaac tccttttctt tgctaaaagg        480
tataaagctg cttttacaga atgttgccaa gctgctgata agctgcctg cctgttgcca        540 aagctcgatg aacttcggga tgaagggaag gcttcgtctg ccaaacagag actcaagtgt       600
gccagtctcc aaaatttgg agaaagagct ttcaaagcat gggcggtggc tcgcctgagc        660
cagagatttc ccaaagctga gtttgcagaa gtttccaagt tagtgacaga tcttaccaaa       720
gtccacacgg aatgctgcca tggagatctg cttgaatgtg ctgatgacag ggcggacctt       780
gccaagtata tctgtgaaaa tcaagattcg atctccagta aactgaagga atgctgtgaa       840
aaacctctgt tggaaaaatc ccactgcatt gccgaagtgg aaaatgatga gatgcctgct       900
gacttgcctt cattagctgc tgattttgtt gaaagtaagg atgtttgcaa aaactatgct       960
gaggcaaagg atgtcttcct gggcatgttt ttgtatgaat atgcaagaag gcatcctgat      1020
tactctgtcg tgctgctgct gagacttgcc aagacatatg aaaccactct agagaagtgc      1080
tgtgccgctg cagatcctca tgaatgctat gccaaagtgt tcgatgaatt taaacctcct      1140
gtggaagagc ctcagaattt aatcaaacaa aattgtgagc tttttgagca gcttggagag      1200
tacaaattcc agaatgcgct attagttcgt tacaccaaga aagtacccca agtgtcaact      1260
ccaactcttg tagaggtctc aagaaaccta ggaaaagtgg gcagcaaatg ttgtaaacat      1320
cctgaagcaa aaagaatgcc ctgtgcagaa gactatctat ccgtggtcct gaaccagtta      1380
tgtgtgttgc atgagaaaac gccagtaagt gacagagtca ccaaatgctg cacagaatcc      1440
ttggtgaaca gcgaccatg cttttcagct ctggaagtcg atgaaacata cgttcccaaa       1500
gagtttaatg ctgaaacatt caccttccat gcagatatat gcacactttc tgagaaggag      1560
agacaaatca gaaacaaac tgcacttgtt gagctcgtga acacaagcc caaggcaaca        1620 aaagagcaac tgaaagctgt tatggatgat ttcgcagctt ttgtagagaa gtgctgcaag      1680
gctgacgata aggagacctg cttcgccgag gagggtaaaa aacttgttgc tgcaagtcaa      1740
gctgccttag gcttatgcag ctgctccccg gtgcacccgc aacaggcgtt ttgcaatgca      1800
gatgtagtga tcagggccaa agcggtcagt gagaaggaag tggactctgg aaacgacatt      1860
tatgcaaacc ctatcaagag gatccagtat gagatcaagc agataaagat gttcaaaggg      1920
cctgagaagg atatagagtt tatctacacg gcccccctcct cggcagtgtg tggggtctcg     1980
ctggacgttg gaggaaagaa ggaatatctc attgcaggaa aggccgaggg ggacggcaag      2040
atgcacatca ccctctgtga cttcatcgtg ccctgggaca ccctgagcac cacccagaag      2100
aagagcctga accacaggta ccagatgggc tgcgagtgca agatcacgcg ctgccccatg      2160
atcccgtgct acatctcctc cccggacgag tgcctctgga tggactgggt cacagagaag      2220
aacatcaacg ggcaccaggc caagttcttc gcctgcatca agagaagtga cggctcctgt      2280
gcgtggtacc gcggcgcggc gcccccaag caggagtttc tcgacatcga ggacccataa       2340
```

```
<210> SEQ ID NO 4
<211> LENGTH: 528
<212> TYPE: DNA
<213> ORGANISM: Artificial Sequence
<220> FEATURE:
<223> OTHER INFORMATION: GAL7 terminater

<400> SEQUENCE: 4
taatgctatt ctagttatgt aagagtggtc ctttccataa aaaaaaaaaa aaagaaaaaa      60 gaatttttagg aatacaatgc agcttgtaag taaaatctgg aatattcata tcgccacaac    120
ttcttatgct tataaaagca ctaatgcctg aatttatgtt gaaaatatgt gtcacaaata    180
aagaaactgt gacatctgac acatttccac tttattgaca agaatagaat ttctttaagt    240
ttcccctcta gattatttat tttcaaattt taggctctgt tgaagtttat tacgtagaaa    300
ttcctacgat agttattagt cctaattgga tgttgcagca aggctcattg tcggtgtcgt    360
tatcgagctt ggcactggcc gtcgttttac aacgtcgtga ctgggaaaac cctggcgtta    420
cccaacttaa tcgccttgca gcacatcccc ccttcgccag ctggcgtaat agcgaagagg    480
cccgcaccga tcgcccttcc caacagttgc gcagcctgaa tggcgaat                 528

<210> SEQ ID NO 5
<211> LENGTH: 30
<212> TYPE: DNA
<213> ORGANISM: Artificial Sequence
<220> FEATURE:
<223> OTHER INFORMATION: HSA cloning forward primer

<400> SEQUENCE: 5
cacgaattcg gcacaatgaa gtgggtaacc                                      30

<210> SEQ ID NO 6
<211> LENGTH: 33
<212> TYPE: DNA
<213> ORGANISM: Artificial Sequence
<220> FEATURE:
<223> OTHER INFORMATION: HSA cloning reward primer

<400> SEQUENCE: 6
cggggagcag ctgcataagc ctaaggcagc ttg                                  33

<210> SEQ ID NO 7
<211> LENGTH: 18
<212> TYPE: DNA
<213> ORGANISM: Artificial Sequence
<220> FEATURE:
<223> OTHER INFORMATION: TIMP2 cloning forward primer

<400> SEQUENCE: 7
tgcagctgct ccccggtg                                                   18

<210> SEQ ID NO 8
<211> LENGTH: 20
<212> TYPE: DNA
<213> ORGANISM: Artificial Sequence
<220> FEATURE:
<223> OTHER INFORMATION: TIMP2 cloning reward primer

<400> SEQUENCE: 8
cgttgaagct ttgcttatgg                                                 20
```

<210> SEQ ID NO 9
<211> LENGTH: 6
<212> TYPE: PRT
<213> ORGANISM: Artificial Sequence
<220> FEATURE:
<223> OTHER INFORMATION: substrate for MMP-2
<220> FEATURE:
<221> NAME/KEY: MOD_RES
<222> LOCATION: (1)
<223> OTHER INFORMATION: (7-methoxycoumarin-4-yl)acetyl Pro
<220> FEATURE:
<221> NAME/KEY: MOD_RES
<222> LOCATION: (4)
<223> OTHER INFORMATION: N-3-(2,4-dinitrophenyl)-L-2,3-diaminopropionyl Leu
<220> FEATURE:
<221> NAME/KEY: MOD_RES
<222> LOCATION: (6)
<223> OTHER INFORMATION: aminated Arg

<400> SEQUENCE: 9

Pro Leu Gly Leu Ala Arg
 1               5

<210> SEQ ID NO 10
<211> LENGTH: 779
<212> TYPE: PRT
<213> ORGANISM: Artificial Sequence
<220> FEATURE:
<223> OTHER INFORMATION: human serum albumin-TIMP2 fusion protein

<400> SEQUENCE: 10

Asp Ala His Lys Ser Glu Val Ala His Arg Phe Lys Asp Leu Gly Glu
 1               5                  10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

-continued

```
Val His Thr Glu Cys Cys His Gly Asp Leu Leu Glu Cys Ala Asp Asp
            245                 250                 255
Arg Ala Asp Leu Ala Lys Tyr Ile Cys Glu Asn Gln Asp Ser Ile Ser
                260                 265                 270
Ser Lys Leu Lys Glu Cys Cys Glu Lys Pro Leu Leu Glu Lys Ser His
            275                 280                 285
Cys Ile Ala Glu Val Glu Asn Asp Glu Met Pro Ala Asp Leu Pro Ser
        290                 295                 300
Leu Ala Ala Asp Phe Val Glu Ser Lys Asp Val Cys Lys Asn Tyr Ala
305                 310                 315                 320
Glu Ala Lys Asp Val Phe Leu Gly Met Phe Leu Tyr Glu Tyr Ala Arg
                325                 330                 335
Arg His Pro Asp Tyr Ser Val Val Leu Leu Leu Arg Leu Ala Lys Thr
            340                 345                 350
Tyr Glu Thr Thr Leu Glu Lys Cys Cys Ala Ala Ala Asp Pro His Glu
        355                 360                 365
Cys Tyr Ala Lys Val Phe Asp Glu Phe Lys Pro Leu Val Glu Glu Pro
    370                 375                 380
Gln Asn Leu Ile Lys Gln Asn Cys Glu Leu Phe Glu Gln Leu Gly Glu
385                 390                 395                 400
Tyr Lys Phe Gln Asn Ala Leu Leu Val Arg Tyr Thr Lys Lys Val Pro
                405                 410                 415
Gln Val Ser Thr Pro Thr Leu Val Glu Val Ser Arg Asn Leu Gly Lys
            420                 425                 430
Val Gly Ser Lys Cys Cys Lys His Pro Glu Ala Lys Arg Met Pro Cys
        435                 440                 445
Ala Glu Asp Tyr Leu Ser Val Val Leu Asn Gln Leu Cys Val Leu His
    450                 455                 460
Glu Lys Thr Pro Val Ser Asp Arg Val Thr Lys Cys Cys Thr Glu Ser
465                 470                 475                 480
Leu Val Asn Arg Arg Pro Cys Phe Ser Ala Leu Glu Val Asp Glu Thr
                485                 490                 495
Tyr Val Pro Lys Glu Phe Asn Ala Glu Thr Phe Thr Phe His Ala Asp
            500                 505                 510
Ile Cys Thr Leu Ser Glu Lys Glu Arg Gln Ile Lys Lys Gln Thr Ala
        515                 520                 525
Leu Val Glu Leu Val Lys His Lys Pro Lys Ala Thr Lys Glu Gln Leu
    530                 535                 540
Lys Ala Val Met Asp Asp Phe Ala Ala Phe Val Glu Lys Cys Cys Lys
545                 550                 555                 560
Ala Asp Asp Lys Glu Thr Cys Phe Ala Glu Glu Gly Lys Lys Leu Val
                565                 570                 575
Ala Ala Ser Gln Ala Ala Leu Gly Leu Cys Cys Ser Cys Ser Pro Val His
            580                 585                 590
Pro Gln Gln Ala Phe Cys Asn Ala Asp Val Val Ile Arg Ala Lys Ala
        595                 600                 605
Val Ser Glu Lys Glu Val Asp Ser Gly Asn Asp Ile Tyr Gly Asn Pro
    610                 615                 620
Ile Lys Arg Ile Gln Tyr Glu Ile Lys Gln Ile Lys Met Phe Lys Gly
625                 630                 635                 640
Pro Glu Lys Asp Ile Glu Phe Ile Tyr Thr Ala Pro Ser Ser Ala Val
                645                 650                 655
```

-continued

```
Cys Gly Val Ser Leu Asp Val Gly Gly Lys Lys Glu Tyr Leu Ile Ala
            660             665             670

Gly Lys Ala Glu Gly Asp Gly Lys Met His Ile Thr Leu Cys Asp Phe
        675             680             685

Ile Val Pro Trp Asp Thr Leu Ser Thr Thr Gln Lys Lys Ser Leu Asn
    690             695             700

His Arg Tyr Gln Met Gly Cys Glu Cys Lys Ile Thr Arg Cys Pro Met
705             710             715             720

Ile Pro Cys Tyr Ile Ser Ser Pro Asp Glu Cys Leu Trp Met Asp Trp
            725             730             735

Val Thr Glu Lys Asn Ile Asn Gly His Gln Ala Lys Phe Phe Ala Cys
            740             745             750

Ile Lys Arg Ser Asp Gly Ser Cys Ala Trp Tyr Arg Gly Ala Ala Pro
        755             760             765

Pro Lys Gln Glu Phe Leu Asp Ile Glu Asp Pro
    770             775
```